(12) United States Patent
Asius et al.

(10) Patent No.: US 8,414,657 B2
(45) Date of Patent: *Apr. 9, 2013

(54) METHOD FOR SUBCUTANEOUS OR INTRADERMAL INJECTION

(75) Inventors: Jerome Asius, Mauguio (FR); Hatem Fessi, Lyons (FR); Franck Gouchet, Donnery (FR); Benedicte Laglenne, Mauguio (FR); Elisabeth Laugher-Laglenne, Paris (FR)

(73) Assignee: Valeant International Bermuda, Hamilton (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,390

(22) Filed: May 21, 2012

(65) Prior Publication Data

US 2012/0231046 A1    Sep. 13, 2012

Related U.S. Application Data

(60) Continuation of application No. 12/776,909, filed on May 10, 2010, now abandoned, which is a continuation of application No. 10/809,349, filed on Mar. 26, 2004, now Pat. No. 7,731,758, which is a division of application No. 09/242,103, filed as application No. PCT/FR98/01241 on Jun. 12, 1998, now Pat. No. 6,716,251.

(30) Foreign Application Priority Data

Jun. 13, 1997 (FR) ................. 97 07334

(51) Int. Cl.
*A61F 2/02* (2006.01)
(52) U.S. Cl. ............ 623/23.75; 623/23.58; 523/113; 604/82; 424/426
(58) Field of Classification Search ........... 623/23.58, 623/23.75; 523/113; 604/82; 424/426
See application file for complete search history.

(56) References Cited

U.S. PATENT DOCUMENTS

| | | | |
|---|---|---|---|
| 2,758,987 A | 8/1956 | Salzberg | |
| 3,773,919 A | 11/1973 | Boswell | |
| 4,093,576 A | 6/1978 | deWijn | |
| 4,166,800 A | 9/1979 | Fong | |
| 4,780,320 A | 10/1988 | Baker | |
| 4,897,267 A | 1/1990 | Bontemps et al. | |
| 4,919,929 A | 4/1990 | Beck | |
| 5,059,123 A | 10/1991 | Jernberg | |
| 5,061,281 A | 10/1991 | Mares et al. | |
| 5,185,152 A | 2/1993 | Peyman | |
| 5,204,382 A | 4/1993 | Wallace et al. | |
| 5,258,028 A | 11/1993 | Ersek et al. | |
| 5,288,496 A | 2/1994 | Lewis | |
| 5,344,452 A | 9/1994 | Lemperle | |
| 5,356,629 A | 10/1994 | Sander et al. | |
| 5,358,475 A | 10/1994 | Mares et al. | |
| 5,447,499 A * | 9/1995 | Allaire et al. ............. | 602/42 |
| 5,451,406 A | 9/1995 | Lawin et al. | |
| 5,466,462 A | 11/1995 | Rosenthal et al. | |
| 5,470,582 A | 11/1995 | Supersaxo et al. | |
| 5,478,837 A | 12/1995 | Rodgers et al. | |
| 5,543,158 A | 8/1996 | Gref et al. | |
| 5,597,897 A | 1/1997 | Ron et al. | |
| 5,599,852 A | 2/1997 | Scopelianos et al. | |
| 5,633,001 A | 5/1997 | Agerup | |
| 5,725,881 A | 3/1998 | Buchholz et al. | |
| 5,977,204 A | 11/1999 | Boyan et al. | |
| 6,534,004 B2 | 3/2003 | Chen et al. | |
| 6,716,251 B1 | 4/2004 | Asius et al. | |
| 7,731,758 B2 * | 6/2010 | Asius et al. ............. | 623/23.75 |

FOREIGN PATENT DOCUMENTS

| | | |
|---|---|---|
| DE | 4235312 | 4/1993 |
| EP | 0134318 | 3/1985 |
| EP | 0251695 | 1/1988 |
| EP | 269921 | 6/1988 |
| EP | 330180 | 8/1989 |
| EP | 0648480 | 4/1995 |
| EP | 0711548 | 5/1996 |
| FR | 2778847 | 11/1999 |
| JP | 07265421 | 10/1995 |
| JP | 8507713 | 8/1996 |
| WO | 93/13755 | 7/1993 |
| WO | 93/15721 | 8/1993 |
| WO | 9402184 | 2/1994 |
| WO | 9421299 | 9/1994 |
| WO | 96/33751 | 10/1996 |
| WO | 99/11196 | 3/1999 |

OTHER PUBLICATIONS

Costantino, et al., "Soft-Tissue Augmentation and Replacement in the Head and Neck", Otolaryngologic Clinics of N.A., pp. 3, 9, 11, vol. 27, No. 1 (Feb. 1994).

R. Kretzschmar, et al., "Experimental Determination of Colloid Deposition Rates and Collision Efficiencies in Natural Porous Media", Water Resources Research, vol. 33, No. 5, pp. 1129-1137, May 1997.

* cited by examiner

*Primary Examiner* — Paul Prebilic
(74) *Attorney, Agent, or Firm* — Oblon, Spivak, McClelland, Maier & Neustadt, L.L.P.

(57) ABSTRACT

The invention concerns an injection implant for filling up wrinkles, thin lines, skin cracks and scars, for reparative or plastic surgery, aesthetic dermatology, and for filling up gums in dental treatment. The invention concerns the use of biologically absorbable polymer microspheres or microparticles suspended in a gel. The suspension is produced either ready-for-use or freeze-dried. The biological absorbability of the microspheres is controlled and enables the production of implants having well defined persistence and deliberately limited to 3 years.

20 Claims, No Drawings

METHOD FOR SUBCUTANEOUS OR INTRADERMAL INJECTION

This application is a continuation of continuation of application Ser. No. 12/776,909 (now abandoned), which is a continuation of application Ser. No. 10/809,349 filed on Mar. 26, 2004 (now U.S. Pat. No. 7,731,758), which is a divisional of application Ser. No. 09/242,103 filed on Feb. 8, 1999 (now U.S. Pat. No. 6,716,251), which was the National Stage of International Application No. PCT/FR98/01241 filed Jun. 12, 1008, and claims priority of application Ser. No. 9/707,334 filed in France on Jun. 13, 1997 under 35 U.S.C. §119. The entire contents of each of the applications Ser. Nos. 10/809, 349, 09/242,103, PCT/FR98/01241, and Ser. No. 9/707,334 are hereby incorporated by reference.

The present invention relates to an implant for subcutaneous or intradermal injection, intended to be used in humans in reparative or plastic surgery and in esthetic dermatology, for filling wrinkles, fine lines, skin cracks, acne scars and other scars, as well as in dentistry for filling the gums.

Up until now, a number of products have been used for this purpose. Each product has advantages and disadvantages.

Silicone gel (or silicone oil) is easy to use. However, the migration of droplets of silicone into the tissues situated below the point of injection, by simple gravity, has been observed after injection. Silicone is frequently the cause of chronic inflammation, of formation of granulomas, and even of tardive allergic reactions. Silicone is not biodegradable, and it is often found in the liver.

Teflon paste is a suspension of polytetrafluoroethylene particles (diameter 10 to 100 µm) in glycerine. This product, in numerous cases, caused severe and chronic serous infections and had to be removed after a few months from dermal and subdermal tissues for most patients. It has also been proved that small polytetrafluoroethylene particles were found in the liver.

Collagen suspensions have been very widely used in the last ten years. The results have however been quite disappointing since collagen is resorbed within 1 to 3 months. Allergic reactions are also noted in about 2% of patients. Finally, it should be noted that collagen is of bovine origin.

Biological samples from the patient himself: the idea was certainly interesting, but clinical experience has shown the failure of the reimplantation of the fatty cells, which are absorbed and disappear within a few weeks.

Another system consisted in adding plasma from the patient to a collagen gelatin of bovine and porcine origin. The results are even more disappointing, and the product is of animal origin.

Hyaluronate gels provided a good alternative by virtue of their biocompatibility and their lack of toxicity. They are moreover widely used in eye surgery. However, their rapid bioresorbability (maximum 2 months) makes them ineffective for use in plastic surgery.

Bioplastics are polymerized silicone particles (diameter 70 to 140 µm) dispersed in polyvinylpyrrolidone. The product had to be withdrawn given the chronic inflammation and the rejection reactions caused by it.

Polymethyl methacrylate (PMHA) microspheres having a diameter of 20 to 40 µm in suspension either in a solution of gelatin or in a solution of collagen. PMMA is not biodegradable, but not enough time has elapsed in order to know what this implant gives after 5 or 6 years. Moreover, the vector remains a solution of collagen of bovine origin, with the problems of allergy which are known for it.

The aim of the invention is to overcome the disadvantages of known products.

The invention uses microspheres or microparticles consisting of a neutral polymer chosen for its innocuousness and which is already widely used by the pharmaceutical industry either by the oral route or by the parenteral route.

The implant according to the invention combines ease of use without prior manipulations, syringeability of the product, resorbability over a controlled time of the polymer as well as of the vector gel, and absence of allergenicity of the product, which makes any preliminary test unnecessary.

The microspheres or microparticles should have a controlled bioresorbability offering a resorbability time of between 1 and 3 years. This means that the polymer will be degraded, after injection in situ, into lowmolecular-weight compounds which will be eliminated from the body by natural processes. In no case does a nonresorbable implant appear to be desirable. It is still a foreign body placed in a living tissue.

The microspheres or microparticles are suspended in a gel. They should have a diameter greater than 5 µm and preferably greater than 20 µm, so as not to be absorbed by the macrophages. They should have a diameter of less than 150 µm, and preferably less than 40 µm, so that, on the one hand, they can be injected by a fine needle and, on the other hand, they do not create a granular mass under the finger.

Two families of polymers essentially meet the preceding definition: the polycaprolactones (and in particular the poly-$\epsilon$-caprolactones), as well as the polylactides (polylactic acids or PLA), the polyglycolides (polyglycolic acids or PGA) and their copolymers (polylactic-co-glycolic acids or PLAGA).

Given the numerous studies already carried out and the good knowledge of the products, in particular as regards the manufacture of microspheres and resorbability, it appears advantageous to use a mixture of polylactic acid (PLA) and polylactic-co-glycolic acid (PLAGA). The proportions of each of these two acids make it possible to determine the persistence of the product.

Numerous trials have also led to a preference for a polymer consisting of a poly-L-lactic acid (crystalline), a poly-D-lactic acid (amorphous), or a mixture of these two acids. Its molecular mass, calculated by viscometry, is advantageously between 70,000 and 175,000 Dalton, and preferably between 120,000 and 170,000 Dalton, an intrinsic viscosity of between 3 and 4 dl/g, and preferably between 3.35 and 3.65 dl/g, a specific rotation of between −150 and −160°, a melting point of between 178.0 and 190.1° C., a heat of fusion of between 85.0 J/g and 90.0 J/g, a quantity of residual solvents <0.01% and a proportion of residual monomer (lactic acid) <0.1%. Such a product is available from PURAC BIOCHEM in Gorinchem (The Netherlands).

Bioresorbable synthetic polymers have been studied for about 15 years under the direction of Michel VERT, Director of Research at C.N.R.S. The first clinical uses of PLAs started in 1981 for various indications in facial traumatology. The use of lactic acid polymers has become systematic in the context of bioresorbable surgical implants. PLAs now have diverse and wide medical applications (bone surgery, maxillo-facial surgery, controlled-release pharmacological formulations: implants, microspheres, nanospheres, vaccines).

The degradation of lactic acid and/or glycolic acid polymers in biological medium occurs exclusively by a chemical mechanism of nonspecific hydrolysis. The products of this hydrolysis are then metabolized and then eliminated by the human body. Chemical hydrolysis of the polymer is complete; the more pronounced its amorphous character and the lower its molecular mass, the more rapidly it occurs. Thus, the resorbability time may be adjusted by acting on the composition of the mixture and/or on the molecular mass of the polymer(s). The biocompatibility of the PLA and PLAGA polymers makes them excellent supports for cellular growth and tissue regeneration.

The microspheres or microparticles are included in a gel. This gel, which is used as vector to maintain the microspheres or microparticles in a homogeneous suspension, is resorbable within approximately 2 months, which corresponds to the time necessary for the creation of fibroses around the microspheres or microparticles. It consists mainly of water for injection and a gelling agent authorized in injection: cellulose derivatives, and more particularly carboxymethylcellulose (CMC) at a concentration by mass of 0.1 to 7.5%, and preferably from 0.1 to 5.0%. It is also possible to use hydroxypropylmethylcellulose (HPMC) which is commonly used in intraocular injections in the context of cataract operations. It is also possible to use a synthetic hyaluronic acid, which is used for intraocular injections and subcutaneous injections. It is also possible to use lactic acid esters, caproic acid esters and the like.

The good dispersion of the microspheres or microparticles and the homogeneity of the gel will be provided by the use of a surfactant chosen for its innocuousness and its authorized subcutaneous and intradermal use. Polyoxyethylene sorbitan monooleate (marketed under the name Tween 80) or pluronic acid will be used.

The product may be provided in ready-for-use prefilled sterile syringes, provided with a needle, or in vials of sterile suspension. It may also be provided in a vial containing a freeze-dried product accompanied by an ampule of sterile water (water for injection), or in a two-compartment prefilled syringe, one containing the freeze-dried product of microspheres or microparticles, the other containing water for injection.

The implant does not require a test of allergenicity. It does not contain any product of animal origin.

The protocol for the manufacture of the implant is described below, in the case of a ready-for-use suspension of microspheres.

A. Preparation of microspheres of lactic acid polymer. The conventional solvent evaporation technique, or the so-called controlled precipitation technique or any other technique which makes it possible to obtain microspheres of the desired size is used.

B. Preparation of a gel of sufficient viscosity to maintain the microspheres in suspension. This viscosity will be adjusted depending on the size of the micro-spheres and the proportion of microspheres dispersed in the gel. This proportion will be from 50 to 300 g/l, and preferably from 60 to 200 g/l.

C. Distribution of the gel into syringes or into vials, in a controlled atmosphere (class $10^4$).

D. Sterilization of the vials or syringes, or use of a process which makes the finished product suitable for injection by the subcutaneous route.

The manufacturing protocol is described below in the case of freeze-dried PLA microparticles, whether this is the L polymer, the D polymer or a mixture thereof.

A. Cryogrinding of the PLA under gaseous nitrogen filtered at 0.22 µm, at a temperature of less than -80° C., on a 100-µm screening grid.

B. Sieving of the microparticles on a 100-µm stainless steel sieve.

C. Preparation of the freeze-drying medium including the dissolution, with stirring, of CMC (gelling agent), of apyrogenic mannitol (cryoprotecting agent), and of polysorbate (surfactant) in water for injection, filtration at 0.22 µm of the solution obtained under gaseous nitrogen filtered at 0.22 µm, and sterilization in an autoclave for 20 minutes at 121.5° C.

D. Distribution of the microparticles at a rate of 100 mg per vial of 4 ml nominal capacity.

E. Distribution of the freeze-drying medium at a rate of 1.05±0.05 g into the vials already containing the polylactic acid microparticles.

F. Dispersion of the microparticles in the freeze-drying medium by an ultrasound dispersion system in order to obtain a homogeneous suspension.

G. Prestoppering of the bottles using pillar stoppers (specific for freeze-drying), rapid freezing below −70° C., storage of the frozen vials below −40° C., and finally freeze-drying and automatic stoppering of the vials.

H. Fitting of capsules and examination of the vials, before sterilization by γ irradiation.

Of course, it is possible to combine the procedures described above, for example in order to obtain a suspension of microparticles ready for use, or a freeze-dried product of microspheres, the microparticles or the microspheres consisting of any of the above-mentioned polymers and mixtures thereof.

EXAMPLE 1

2 g of PLA are dissolved in 20 ml of an organic solvent (ethyl acetate). This solution is dispersed in 100 ml of water containing 5 g of polyoxyethylene sorbitan monooleate. Moderate vortex stirring is maintained until evaporation of the solvent and formation of microspheres having a mean diameter of 40 µm. The microspheres formed are recovered by sedimentation, filtration and drying. They are then included in a gel consisting of water and CMC (0.5% by mass). After moderate stirring, the distribution is carried out.

EXAMPLE 2

2 g of PLA are dissolved in 20 ml of an organic solvent (methylene chloride). This solution is dispersed in 100 ml of water containing 5 g of polyoxyethylene sorbitan monooleate. Moderate vortex stirring is maintained until evaporation of the solvent and formation of microspheres having a mean diameter of 80 µm. The micro- spheres formed are recovered by sedimentation, filtration and drying. They are then included in a gel consisting of water and CMC (0.5% by mass). After moderate stirring, the distribution is carried out.

EXAMPLE 3

2 g of PLA are dissolved in 20 ml of an organic solvent (chloroform). This solution is dispersed in 100 ml of water containing 5 g of polyoxyethylene sorbitan monooleate. Moderate vortex stirring is maintained until evaporation of the solvent and formation of microspheres having a mean diameter of 50 µm. The micro- spheres formed are recovered by sedimentation, filtration and drying. They are then included in a gel consisting of water and HPMC (1% by mass). After moderate stirring, the distribution is carried out.

EXAMPLE 4

600 g of polylactic acid are cryoground to a final particle size of between 20 and 100 µm, with a median at 40 µm. These microparticles are distributed at a rate of 100 mg per vial.

6.5 kg of freeze-drying medium are manufactured by dissolving 97.5 g of sodium CMC, 276.25 g of apyrogenic mannitol, and 6.5 g of polysorbate 80 in qs 6.5 liters of water for injection. This medium is distributed at a rate of 1 g per vial.

Trials were carried out on animals (hairless mice and New Zealand rabbits) with the products of Examples 1 to 4. The results are identical, and during the first two months, and from the eighth day after the injection, the appearance of giant cells surrounding in a network the crystals of polylactic acid is observed followed by their transformation by creation of a fibrosis which reconstitutes the subcutaneous tissue.

What is claimed is:

1. A method of performing reparative or esthetic dermatologic surgery, the method comprising
   subcutaneously or intradermally injecting into a subject a bioresorbable injectable implant consisting essentially of bioresorbable microspheres or microparticles suspended in a gel consisting essentially of a material of non-animal origin,
   wherein said microspheres or microparticles consist of at least one polymer of non-animal origin selected from the group consisting of lactic acid polymers, glycolic acid polymers, and lactic acid-glycolic acid co-polymers.

2. The method according to claim 1, wherein said surgery is for filling wrinkles, fine lines, skin cracks or scars.

3. The method according to claim 1, wherein said surgery is for filling the gums for dentistry.

4. The method according to claim 1, wherein said implant consists essentially of materials of non-animal origin.

5. The method according to claim 1, wherein said microspheres or microparticles have a mean diameter greater than 5 μm and less than 150 μm.

6. The method according to claim 1, wherein said microspheres or microparticles have a mean diameter greater than 20 μm and less than 80 μm.

7. The method according to claim 1, wherein said microspheres or microparticles have a mean diameter greater than 20 μm and less than 40 μm.

8. The method according to claim 1, wherein said polylactic acid has a molecular mass of between 70,000 and 175,000 Daltons.

9. The method according to claim 1, wherein said polylactic acid has a molecular mass of between 120,000 and 170,000 Daltons.

10. The method according to claim 1, wherein said polylactic acid has an intrinsic viscosity of between 3 and 4 dl/g.

11. The method according to claim 1, wherein said polylactic acid has an intrinsic viscosity of between 3.35 and 3.65 dl/g.

12. The method according to claim 1, wherein said microspheres or microparticles are present in said gel at a concentration of from 50-300 g/l., as weight of said microspheres or microparticles per volume of gel.

13. The method according to claim 12, wherein said microspheres or microparticles are present in said gel at a concentration of from 60-200 g/l.

14. The method according to claim 1, wherein said gel consists essentially of water, from about 0.1 to about 7.5% (wt/wt) of an injectable gelling agent, and a surfactant.

15. The method according to claim 1, wherein said gel consists essentially of water and 0.1 to 7.5% by weight carboxymethylcellulose (CMC) or hydroxypropylmethylcellulose.

16. The method according to claim 14, wherein said gelling agent is a cellulose derivative.

17. The method according to claim 16, wherein said cellulose derivative is selected from the group consisting of carboxymethylcellulose and hydroxypropylmethylcellulose.

18. The method according to claim 14, wherein said gelling agent is synthetic hyaluronic acid.

19. The method according to claim 14, wherein said surfactant is selected from the group consisting of polyoxyethylene sorbitan monooleate and pluronic acid.

20. The method according to claim 1, wherein said microparticles consist of a polymer selected from the group consisting of poly-L-lactic acid, poly-D-lactic acid, and mixtures thereof.

* * * * *